US012797035B2

(12) United States Patent
Chi et al.

(10) Patent No.: US 12,797,035 B2
(45) Date of Patent: Nov. 17, 2026

(54) PORTABLE NON-INVASIVE INTRACRANIAL PRESSURE SENSOR

(71) Applicants: William Marsh Rice University, Houston, TX (US); Baylor College of Medicine, Houston, TX (US)

(72) Inventors: Taiyun Chi, Houston, TX (US); Matt Y. Cheung, Houston, TX (US); Gerald Topalli, Houston, TX (US); Ashok Veeraraghavan, Houston, TX (US); Mohammad Hirzallah, Houston, TX (US)

(73) Assignees: William Marsh Rice University, Houston, TX (US); Baylor College of Medicine, Houston, TX (US)

( * ) Notice: Subject to any disclaimer, the term of this patent is extended or adjusted under 35 U.S.C. 154(b) by 1 day.

(21) Appl. No.: 19/047,399

(22) Filed: Feb. 6, 2025

(65) Prior Publication Data

US 2025/0261925 A1 Aug. 21, 2025

Related U.S. Application Data

(60) Provisional application No. 63/554,704, filed on Feb. 16, 2024.

(51) Int. Cl.

| | |
|---|---|
| ***A61B 8/06*** | (2006.01) |
| ***A61B 8/00*** | (2006.01) |
| ***A61B 8/08*** | (2006.01) |

(52) U.S. Cl.

CPC .......... *A61B 8/0808* (2013.01); *A61B 8/4209* (2013.01); *A61B 8/5223* (2013.01)

(58) Field of Classification Search

CPC .... A61B 8/0808; A61B 8/4209; A61B 8/5223

See application file for complete search history.

(56) References Cited

U.S. PATENT DOCUMENTS

| | | | | |
|---|---|---|---|---|
| 8,603,014 | B2 | 12/2013 | Alleman et al. | |
| 9,568,890 | B1 * | 2/2017 | Kim | H03L 7/0814 |
| 11,166,696 | B2 | 11/2021 | Michaeli et al. | |
| 2009/0198137 | A1 * | 8/2009 | Ragauskas | A61B 8/0808 600/449 |
| 2012/0108918 | A1 * | 5/2012 | Jarvik | A61B 5/4827 600/301 |
| 2017/0230017 | A1 * | 8/2017 | Hori | H03F 3/2171 |
| 2019/0033431 | A1 * | 1/2019 | Haneda | G01S 17/06 |
| 2022/0006459 | A1 * | 1/2022 | Bautista Gabriel | H03K 19/01759 |

(Continued)

FOREIGN PATENT DOCUMENTS

| | | | | |
|---|---|---|---|---|
| WO | WO-2022123254 | A1 * | 6/2022 | H03F 3/2173 |
| WO | 2023/196190 | A1 | 10/2023 | |

*Primary Examiner* — Patricia J Park

(74) *Attorney, Agent, or Firm* — Osha Bergman Watanabe & Burton LLP

(57) ABSTRACT

A system for non-invasive intracranial pressure (ICP) sensing includes a signal generator that generates a series of pulses, an ultrasound transmitter that emits an ultrasound waveform based on the series of pulses, an ultrasound receiver that receives the ultrasound waveform, and a time of flight (ToF) measurement unit configured to determine a change in a temporal delay between the series of pulses and the received ultrasound waveform. A head of a patient is disposed between the ultrasound transmitter and the ultrasound receiver.

13 Claims, 7 Drawing Sheets

(56) References Cited

U.S. PATENT DOCUMENTS

| | | | | |
|---|---|---|---|---|
| 2022/0160327 | A1 | 5/2022 | Sutton et al. | |
| 2022/0409080 | A1 | 12/2022 | Kyriacou et al. | |
| 2025/0261923 | A1 * | 8/2025 | Perez | A61B 8/56 |

* cited by examiner

| | |
|---|---|
| $C_{S1,2}$ | 620pF |
| $C_F$ | 750uF |
| $L + L_F$ | 150uH |
| Cm | 750nF |
| Lm | 57.6uH |

PORTABLE NON-INVASIVE INTRACRANIAL PRESSURE SENSOR

CROSS-REFERENCE TO RELATED APPLICATIONS

This application claims priority to and the benefit of the filing date of U.S. Provisional Patent Application 63/554,704, filed on Feb. 16, 2024, which is hereby incorporated by reference herein in its entirety.

STATEMENT REGARDING FEDERALLY SPONSORED RESEARCH OR DEVELOPMENT

This invention was made with government support under Grant Number W81XWH-21-9-0016 awarded by the Defense Health Agency, Medical Research and Development Branch. The government has certain rights in the invention.

BACKGROUND

Intracranial pressure (ICP) is a critical physiological parameter that provides key insights into the condition of the intracranial region. ICP monitoring is critical for managing various neurological conditions. Clinicians routinely use ICP monitoring in neurovascular intensive care units (neuro-ICUs) because it provides actionable and timely information for patient care.

Conventionally, neurosurgeons measure ICP through invasive methods. A first method involves drilling into the skull to insert a catheter into the brain ventricle. This technique allows for both pressure monitoring and cerebrospinal fluid (CSF) drainage, providing dual benefits in managing elevated ICP. A second method that involves an intraparenchymal bolt requires placing a hollow screw in the skull to insert a pressure sensor into the brain parenchyma. Due to the invasive nature of these procedures, ICP monitoring must be performed by experienced healthcare professionals. Additionally, the complexity and potential complications of these techniques underscore the need for less invasive yet equally accurate methods of ICP assessment to expand their accessibility especially at the site of injury and improve patient outcomes.

Significant efforts have been made to develop non-invasive or minimally invasive methods for ICP monitoring. One such approach combines transcranial Doppler (TCD) with arterial blood pressure (ABP) measurements to formulate a mathematical model for estimating mean ICP. This method leverages the relationship between cerebral blood flow (CBF) velocity and systemic blood pressure to provide an indirect estimate of ICP. The drawback of this method is that the model is patient-specific and requires a large training dataset. Secondly, advancements in ultrasound imaging technologies have enabled the measurement of optic sheath diameter, where changes in its diameter correlate with changes in ICP. However, this diagnosis is patient-specific, and it does not yield a very conclusive result. Invasive follow up procedures are required to confirm the diagnosis. Thirdly, ICP detection with near-infrared spectroscopy has been attempted. Using a set of physically relevant features and machine learning algorithms, they correlated the morphological changes in the CBF waveform with underlying ICP baselines. This approach enables an estimation of ICP from non-invasive cerebral blood flow sensing. However, this method is also patient-dependent and requires a large training dataset.

Non-invasive methods for measuring ICP that overcome the above limitations would be beneficial. Such non-invasive methods would be particularly useful when available in a portable device that can be used even in non-clinical settings.

SUMMARY

In general, in one aspect, one or more embodiments relate to a system for non-invasive intracranial pressure (ICP) sensing, comprising: a signal generator that generates a series of pulses; an ultrasound transmitter that emits an ultrasound waveform based on the series of pulses; an ultrasound receiver that receives the ultrasound waveform, wherein a head of a patient is disposed between the ultrasound transmitter and the ultrasound receiver; and a time of flight (ToF) measurement unit configured to determine a change in a temporal delay between the series of pulses and the received ultrasound waveform.

In general, in one aspect, one or more embodiments relate to a method for non-invasive intracranial pressure (ICP) sensing, comprising: generating, by a signal generator, a series of pulses; emitting, by an ultrasound transmitter an ultrasound waveform based on the series of pulses; receiving, by an ultrasound receiver, the ultrasound waveform, wherein a head of a patient is disposed between the ultrasound transmitter and the ultrasound receiver; and determining, by a time of flight (ToF) measurement unit, a change in a temporal delay between the series of pulses and the received ultrasound waveform.

Other aspects of the invention will be apparent from the following description and the appended claims.

DETAILED DESCRIPTION

Figure 1:
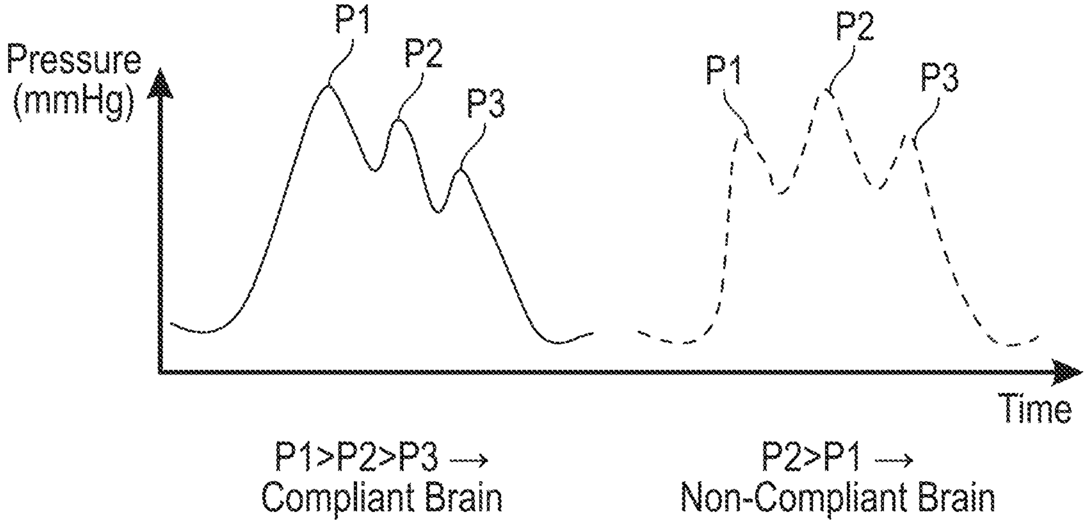
FIG. 1 shows waveforms of intracranial pressure according to some embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

In a compliant brain, any increase in the volume of one component must be offset by a decrease in another to maintain normal ICP. Normally, ICP waveform morphology contains three peaks (P1, P2, P3), triggered by the cardiac cycle, in a decreasing order for a healthy patient. However, slight increases in volume due to bleeding, swelling, or tumor growth can elevate ICP and significantly alter the ICP waveform morphology, particularly increasing the P2/P1 amplitude ratio, as illustrated in FIG. 1, showing examples of waveforms of a healthy compliant brain in the left panel and a non-compliant brain in the right panel. A loss of brain compliance may prevent the brain from compensating for additional volume and maintaining normal pressure. A non-compliant brain can result in severe neurological impairment or life-threatening conditions, often requiring immediate neurosurgical intervention. Therefore, ICP monitoring has become a routine diagnostic tool in neurosurgery and critical care settings. Continuous monitoring of ICP allows healthcare providers to detect early signs of intracranial hypertension and other abnormalities, enabling timely interventions.

Figure 2:
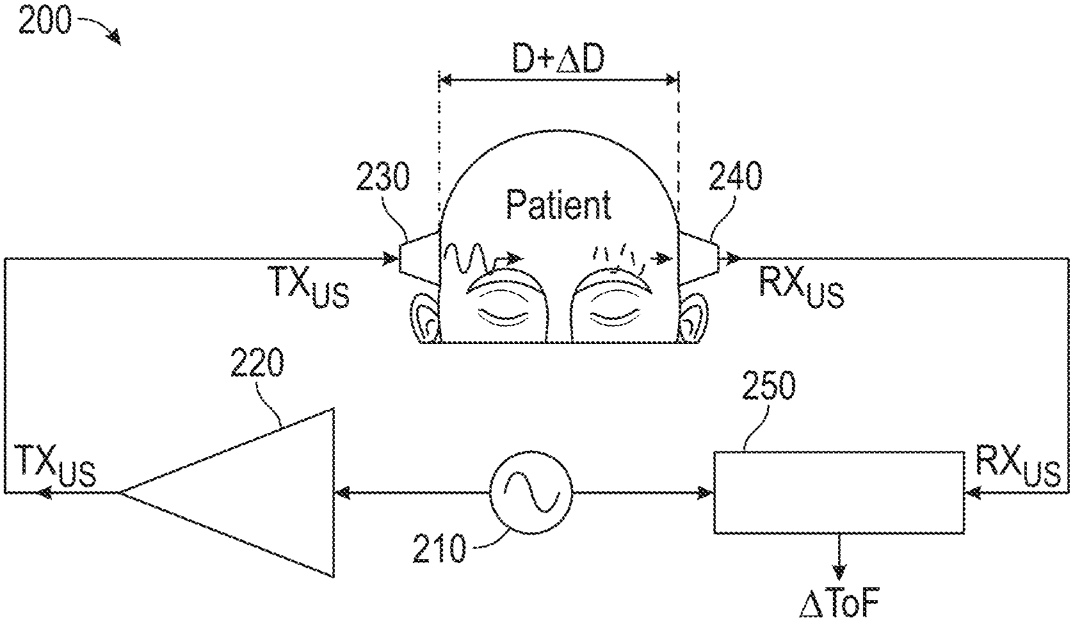
FIG. 2 shows a system for non-invasive measurement of intracranial pressure according to some embodiments.

Recent technological advancements have challenged the longstanding notion that the cranial cavity is rigid and nonexpandable. Contrary to this traditional understanding, modern studies have revealed a correlation between ICP and the capacity for cranial expansion. Notably, fluctuations in ICP during the cardiac cycle can induce changes in the cranial cavity's diameter D by approximately $\Delta D=15$ μm, as illustrated in FIG. 2. This discovery underscores ΔD monitoring by tracking these subtle expansions.

Embodiments disclosed herein generally relate to systems for non-invasive measurement of intracranial pressure, e.g., as shown in FIG. 2. In some embodiments, the system 200 includes a signal generator 210 that generates a series of pulses. The series of pulses may be processed by a power amplifier 220 that generates a driving signal $TX_{US}$ based on the series of pulses. $TX_{US}$, in some embodiments, is used to drive an ultrasound transmitter 230 to emit an ultrasound waveform. The ultrasound waveform propagates through the head of the patient and is received by an ultrasound receiver 240 that generates a received signal $RX_{US}$. In some embodiments, a time delay measurement unit 250 then determines the temporal delay between $TX_{US}$ and $RX_{US}$. The temporal delay depends on the distance D between the ultrasound transmitter 230 and the ultrasound receiver 240. With increasing distance D (e.g., $D+\Delta D$), the time of flight (ToF) for the ultrasound waveform traveling from the ultrasound transmitter 230 to the ultrasound receiver 240 increases. Accordingly, based on the temporal delay, the distance D may be determined. Assuming that both the ultrasound transmitter and the ultrasound receiver are directly disposed against the head of the patient (e.g., with the head of the patient between ultrasound transmitter and ultrasound receiver, and the transmitter and receiver disposed over the opposing temporal bone windows), the distance D changes as the cranial cavity expands and contracts. The ICP may then be derived, based on D, for example, to determine whether the ICP is indicative of a compliant healthy brain (FIG. 1, left panel) or a non-compliant brain (FIG. 1, right panel).

Each of the components of the system 200 are subsequently described after a brief discussion of the benefits of the system 200.

Embodiments of the disclosure have one of more of the following benefits. Embodiments of the disclosure use constant frequency signals to determine a distance (or change in distance) based on the change of the temporal delay or the change of the ToF. Unlike other approaches that use variable frequency phase measurements, embodiments of the disclosure are not susceptible to frequency-dependent phase errors originating from transducers, electronics, and the intrinsic properties of the brain and skull. By utilizing a through-transmission-based approach (with the head of the patient disposed between the ultrasound transmitter and the ultrasound receiver), internal reflections are not a concern, as they always arrive later than the main path. This is not true for other approaches that use a round-trip signal (with the ultrasound transmitter and the ultrasound receiver disposed on the same side of the patient's head). A high dynamic range time-to-digital converter (TDC) (discussed below) is used to implement the ToF measurement unit with a very high accuracy, thereby producing accurate estimates of ΔD and ΔICP. To drive the ultrasound transmitter with high efficiency, a Class-DE power amplifier (PA) (discussed below) with a high output swing and close to 95% efficiency is used to implement the power amplifier 220.

These features collectively address the limitations of current ICP monitoring methods, enabling a more accurate, reliable, and portable non-invasive ICP sensor.

Ultrasound Frequency Selection

The choice of ultrasound frequency involves selecting an appropriate transducer, while balancing trade-offs such as ultrasonic attenuation and transducer size. Due to the highly attenuative nature of the cranial region, a lower ultrasound frequency may be preferred to ensure effective transmission. On the other hand, a lower frequency usually leads to a larger transducer footprint and compromised sensing resolution. To optimize this balance, experiments were conducted using transducers operating at various frequencies on an adult head phantom (True Phantom Solutions HD-A03). The measurement results indicate that for the same amount of power (~36 mW) delivered to the transducers, the ultrasound wave generated by a 1 MHz transducer cannot penetrate the skull due to significant attenuation and reflection. On the other hand, by using a transducer that operates at a lower frequency of, for example, ~560 kHz, the ultrasound wave successfully penetrates the skull and provides a reasonable Signal-to-Noise Ratio (SNR) at the RX side. Consequently, a transducer with an operating frequency of ~560 kHz (for example, BB-BMD500KTR) was chosen. The diameter of this transducer is 25 mm, which is compact enough for portable applications. Other frequencies that may be associated with different tradeoffs for penetration depth, power requirements, resolution, etc., may be used without departing from the disclosure.

Timing Control

Signal generator 210 may be understood as part of a global timing control that manages the timing for entire system 200, including transmission, receiving, and processing of the ultrasound waveform, as subsequently discussed.

Figure 3A:
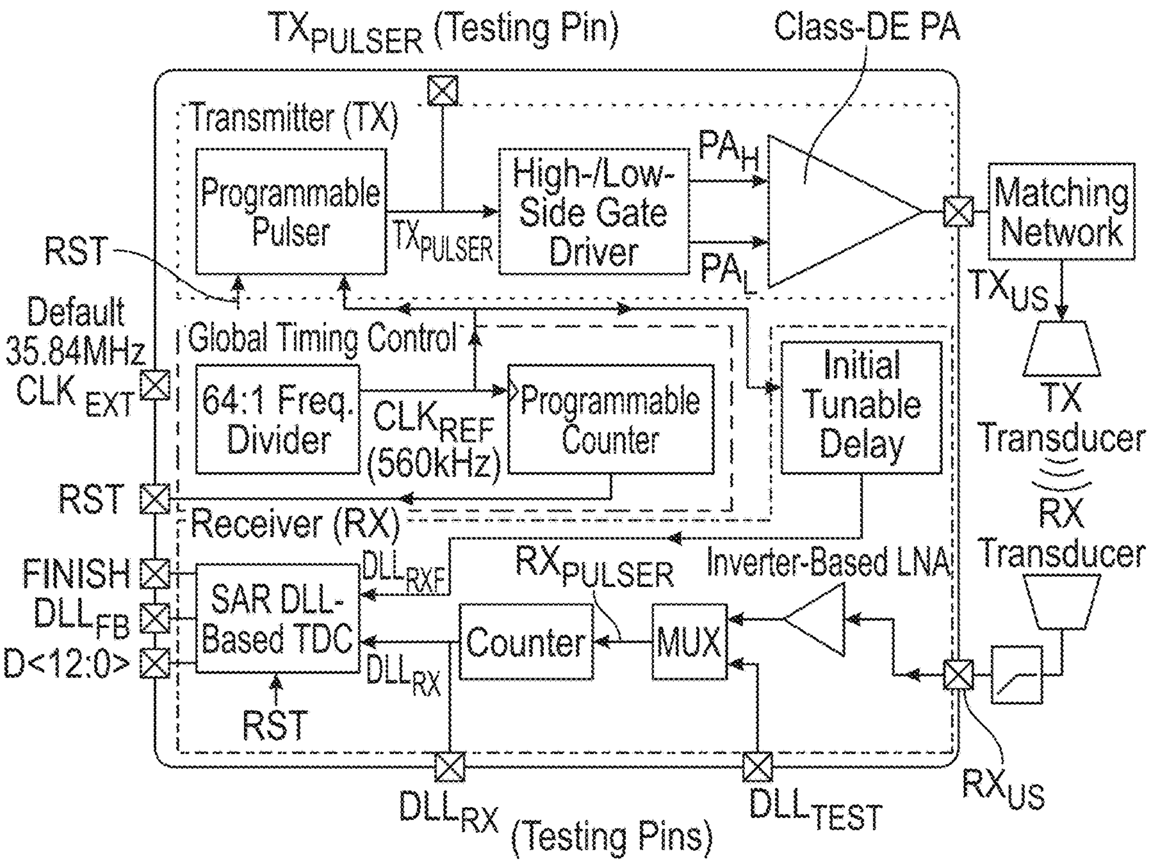
FIG. 3A shows a system diagram of a system for non-invasive measurement of intracranial pressure according to some embodiments.
Figure 3B:
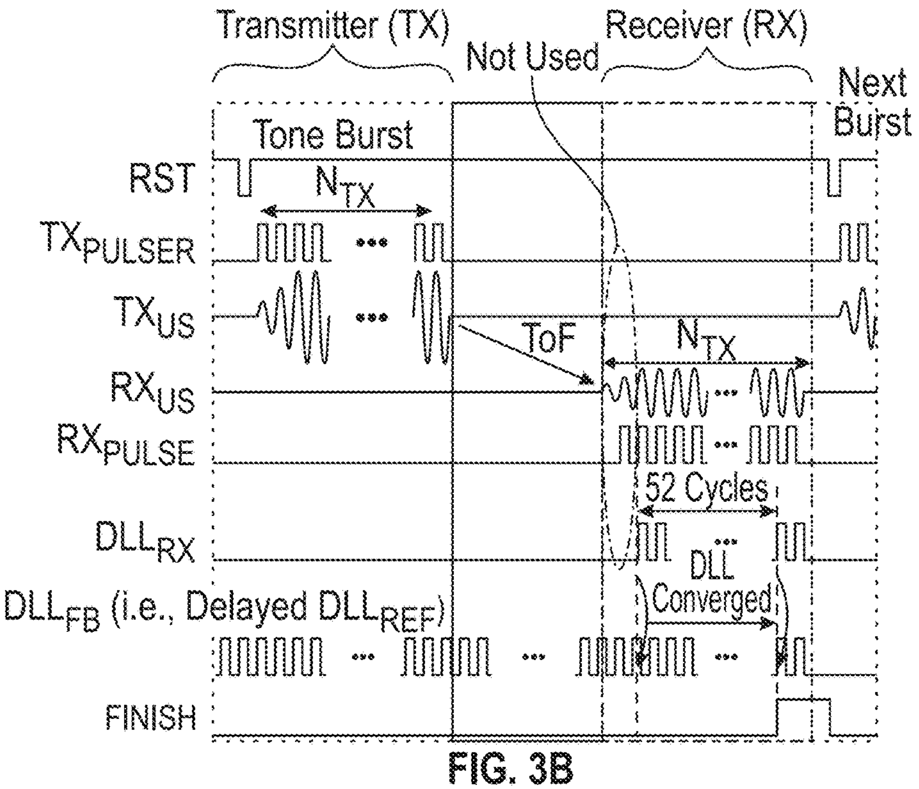
FIG. 3B shows a timing diagram of a system for non-invasive measurement of intracranial pressure according to some embodiments.

The timing diagram of FIG. 3B outlines a sequence of operations for an acquisition cycle. The timing diagram is subsequently discussed in conjunction with the system diagram 3A. The system diagram is specific to a particular implementation of the system as introduced more broadly in reference to FIG. 2. Accordingly, certain elements are of a particular type. For example, a Class-DE Power Amplifier (PA) is used to implement the power amplifier 220. Other elements (e.g. a different type of power amplifier) may be used without departing from the disclosure. The process begins with the global and timing control issuing an RST signal, initiating the measurement. On the TX side, a programmable pulser (e.g., signal generator 210) generates a series of pulses that activate the Class-DE PA, driving the TX transducer. The resulting TX burst propagates through the medium for a duration defined by the ToF.

Upon reaching the RX transducer, the signal is filtered by a first-order RC high-pass filter (implemented off-chip) and then amplified by a low noise amplifier (LNA). A counter is used to skip the initial few cycles of $RX_{PULSE}$ (identified by "Not Used" in the timing diagram) to prevent errors caused by the settling times of the TX and RX. For example, the TX may require approximately 10 cycles to reach a steady state, while the RX may stabilize within 2 to 3 cycles. In one implementation, close to 100 cycles are discarded to allow sufficient time for both TRX settling and internal reflections to dissipate. The delay change of the DLLRX is measured by a time-to-digital converter (TDC), which takes 52 cycles to converge. Once converged, a FINISH signal is issued, indicating that an SAR codeword (discussed below) indicative of the ToF is ready to be streamed out of the chip.

TX Design Specifications

The measured signal attenuation of the ultrasound waveform from the ultrasound transmitter 230 to the ultrasound receiver 240, over a distance of approximately ~15 cm may be assumed to be 43 dB at 560 kHz. This loss results from several factors, including reflections at the skull, attenuation within the intracranial space, and potential losses in the transducer itself. Accordingly, to deliver ~100 $mV_{PP}$ at the RX input for a reasonable SNR, a voltage swing of ~15 $V_{PP}$ is required at the TX output. In some embodiments, an impedance down-transformation network is adopted between the PA 220 output and the TX 230 transducer to reduce the required PA output voltage. This may help address voltage breakdown limitations known to exist in bulk CMOS processes, which would otherwise make it difficult to achieve 15 $V_{PP}$. Further, in some embodiments, a cascode PA topology is used to enables a doubled PA output swing with a reduced impedance transformation ratio to decrease the matching network loss. To further minimize the PA power consumption, a switching-mode Class-DE PA topology, which offers high efficiency at the operating frequency, may be used. In one implementation, the power transmitted by the TX transducer is 1.03 $mW/cm^2$, which is 91× lower than the FDA limit for cranial ultrasound applications (94 $mW/cm^2$).

RX Design Specifications

ICP pulsations can result in a maximum change in ΔD of 15 μm. Given the ultrasonic velocity of 1550 m/s, the maximum ΔToF is approximately 9.6 ns. To ensure sufficient margin and to prevent TDC saturation due to potential movement artifacts from patients, the maximum detection range of our TDC in some embodiments, is designed to be ~100 ns. Additionally, to achieve a high resolution in ΔD measurement for accurate monitoring of the P2/P1 ratio, in some embodiments, a TDC resolution of 64 ps, corresponding to 0.1 μm resolution in ΔD is chosen. These specifications lead to the TDC dynamic range requirement of $$20\log\left(\frac{100\text{ ns}}{64\text{ ps}}\right) = 64\text{ dB}.$$

Despite the large dynamic range, due to the full range of the TDC (i.e., ~100 ns) being smaller than the period of the ultrasound signal (i.e., ~1.8 ms), there is a high chance that the received signal at the start of the measurement could fall outside the TDC range. To address this issue, in some embodiments, an SPI-controlled initial tunable delay (see FIGS. 3A, 3B) is implemented to calibrate the delay difference between the received signal ($DLL_{RX}$) and the internal reference clock signal ($DLL_{REF}$), bringing the delay difference within the TDC convergence range. Based on the TX and TDC specifications, the required specifications for the LNA may be derived. For a 15 $V_{PP}$ signal applied to the TX transducer, the signal strength at the RX input is approximately 100 $mV_{PP}$. The LNA needs to amplify this signal to full swing (e.g., 1.8 $V_{PP}$) while ensuring the jitter remains below the required resolution of the system.

Example Circuit Implementation

Based on the ultrasound frequency selection, and the TX and RX design specifications, in some embodiments the following example circuit implementations may be used. The described components may then be integrated in the system diagram of FIG. 3A and may be operated based on the timing diagram of FIG. 3B.

Power Amplifier (PA)

Figure 4A:
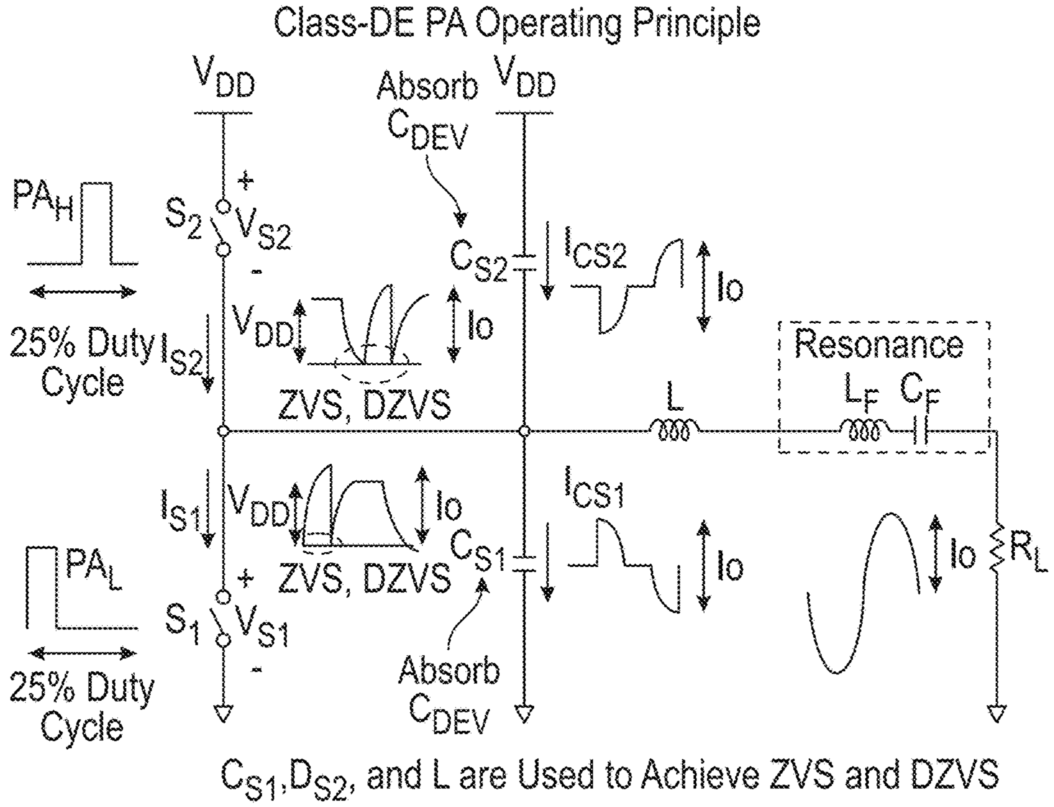
FIG. 4A shows a diagram of the operating principle of a Class-DE power amplifier according to some embodiments.

In some embodiments, a Class-DE PA is used to drive the TX transducer. FIG. 4A shows the schematics of a Class-DE PA. The Class-DE PA includes two switches ($S_1$ and $S_2$), two shunt capacitors ($C_{S1}$, $C_{S2}$), and a matching network (L, $L_F$ and $C_F$). The Class-DE operation is enabled by introducing Zero Voltage Switching (ZVS) and Zero Voltage Slope Switching (DZVS) as in a Class-E PA to a conventional Class-D amplifier and adjusting the duty cycle to 25%, as illustrated in FIG. 4A. The use of Class-DE PA offers at least two advantages. First, it exhibits higher efficiency than Class-D at the chosen operating frequency, as the transistor parasitic capacitances ($C_{DEV}$), which limit the efficiency of Class-D PAs, are absorbed by the two shunt capacitors ($C_{S1}$ and $C_{S2}$). Second, while the drain voltage swing can exceed $3\times V_{DD}$ for a Class-E PA, it is limited to $V_{DD}$ for a Class-DE PA. This allows the use of a higher $V_{DD}$ for higher output power and efficiency without compromising the transistor reliability as in Class-E PA. The power delivered by a Class-DE PA to the load $R_L$ in FIG. 4A is given as $$P_{out} = \frac{V_{DD}^2}{2R_L\pi^2}. \quad (1)$$

This equation indicates that increasing the output power can be achieved by increasing the supply voltage ($V_{DD}$) and reducing the impedance presented to the power cell. In some embodiments, cascode switches are used to implement $S_1$ and $S_2$ to boost $V_{DD}$ from 3.3 to 6.6 V. Furthermore, the transducer impedance at the operating frequency is relatively high (~850Ω), which limits the maximum output power. To mitigate this, an off-chip matching network down-converts the high transducer impedance to 62Ω, which is the optimum load impedance of the PA. The component values of the matching network that may be used are shown in FIG. 4B (bottom right).

Figure 4B:
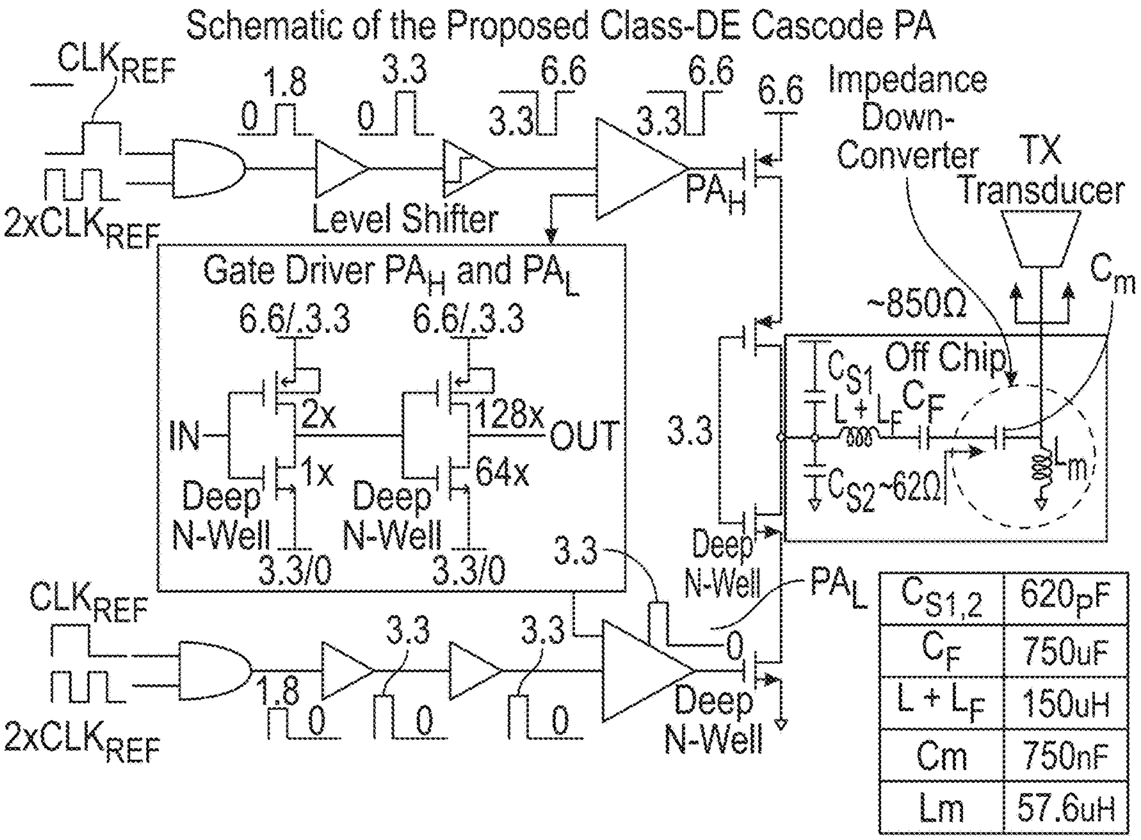
FIG. 4B shows a diagram of transistor-level implementation of a Class-DE power amplifier according to some embodiments.

To ensure the cascode switches are correctly driven without reliability concerns, two sets of level shifters and drivers are designed to drive the top PMOS switch and the bottom NMOS switch, as shown in FIG. 4B. First, the 25% duty cycle signal is generated by an AND gate with $CLK_{REF}$ and $2\times CLK_{REF}$ as its inputs. Next, this 25% duty cycle signal passes through a level shifter and a gate driver. The difference between the two sets of level shifters and drivers is that the high-side circuits toggle between 3.3 and 6.6 V, while the low-side circuits toggle between 0 and 3.3 V. All NMOS transistors are implemented in the deep N well. The delays of the gate drivers are designed and simulated to ensure the correct timing in driving the PA switches.

SAR DLL-Based TDC

Figure 5:
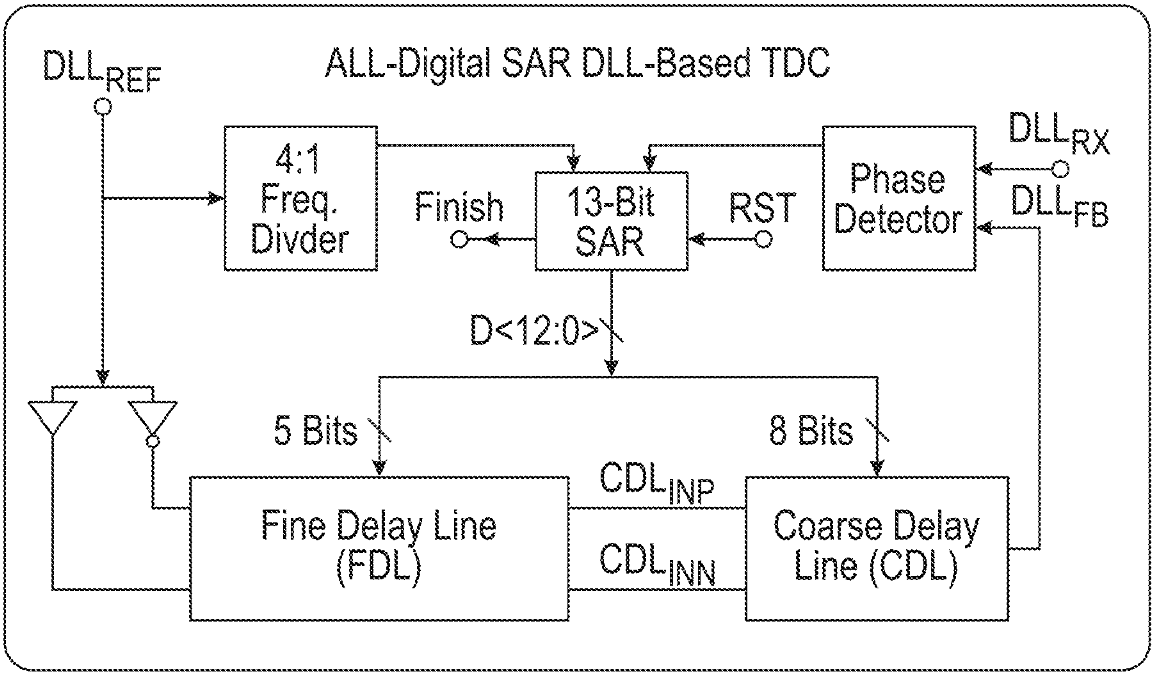
FIG. 5 shows a diagram of a successive approximation register (SAR) delay-locked loop (DLL)-based time-to-digital converter (TDC) according to some embodiments.

A TDC is used to measure ΔToF. The most straightforward TDC topology is the flash TDC, consisting of a delay line formed by buffers and DFFs. In this architecture, a START signal initiates the measurement and propagates through the buffers and DFFs. When the STOP signal is received, the data stored at the DFF outputs is converted to the actual delay difference using a thermometer-to-binary encoder. The delay resolution of this TDC is determined by the delay of a single buffer. However, to achieve a large dynamic range, the TDC requires a significant number of unit delays and DFFs, leading to an increased area and power consumption. Other types of TDCs, such as the Vernier TDC, face similar challenges in terms of area and power efficiency. To address this challenge, in some embodiments, a successive approximation register (SAR) DLL-based TDC, as shown in FIG. 5, is employed. The reference DLL signal ($DLL_{REF}$) is initially converted to differential before being delayed by a 5-bit fine differential delay line (FDL) and an 8-bit differential coarse delay line (CDL). The output of the delay line ($DLL_{FB}$) is then compared with the TDC input ($DLL_{RX}$) using a phase detector. This phase detector checks whether the delayed reference signal ($DLL_{FB}$) leads $DLL_{RX}$ and drives the SAR controller toward minimizing the delay difference between them. Unlike traditional TDCs, this architecture utilizes significantly fewer DFFs, thereby achieving a high dynamic range without penalties in the area or power consumption.

Figure 6:
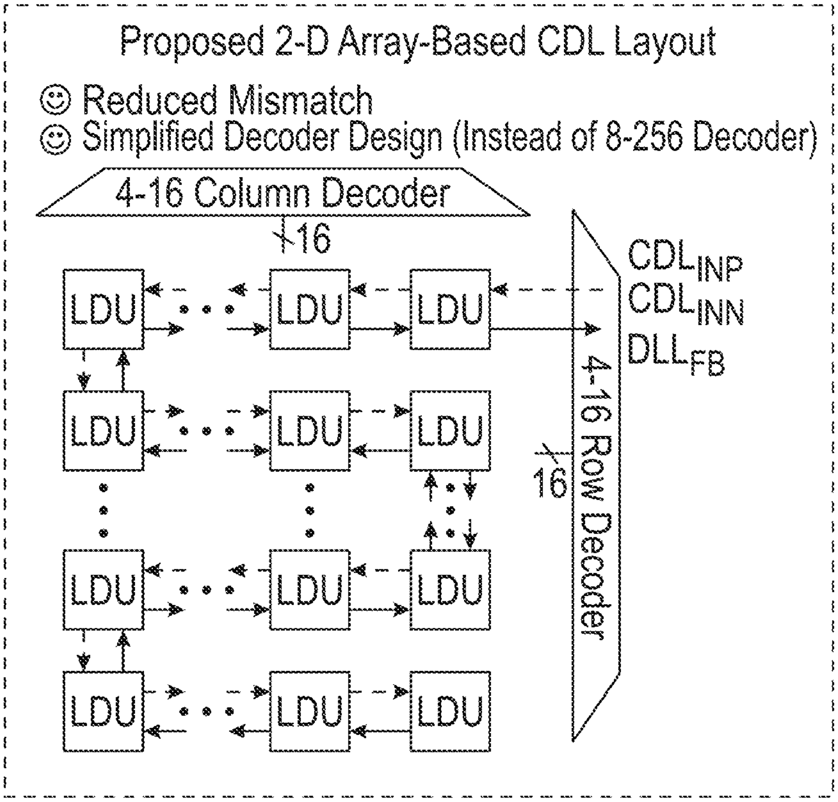
FIG. 6 shows a diagram of latticed delay units (LDUs) distributed in a 2D matrix according to some embodiments.
Figure 7:
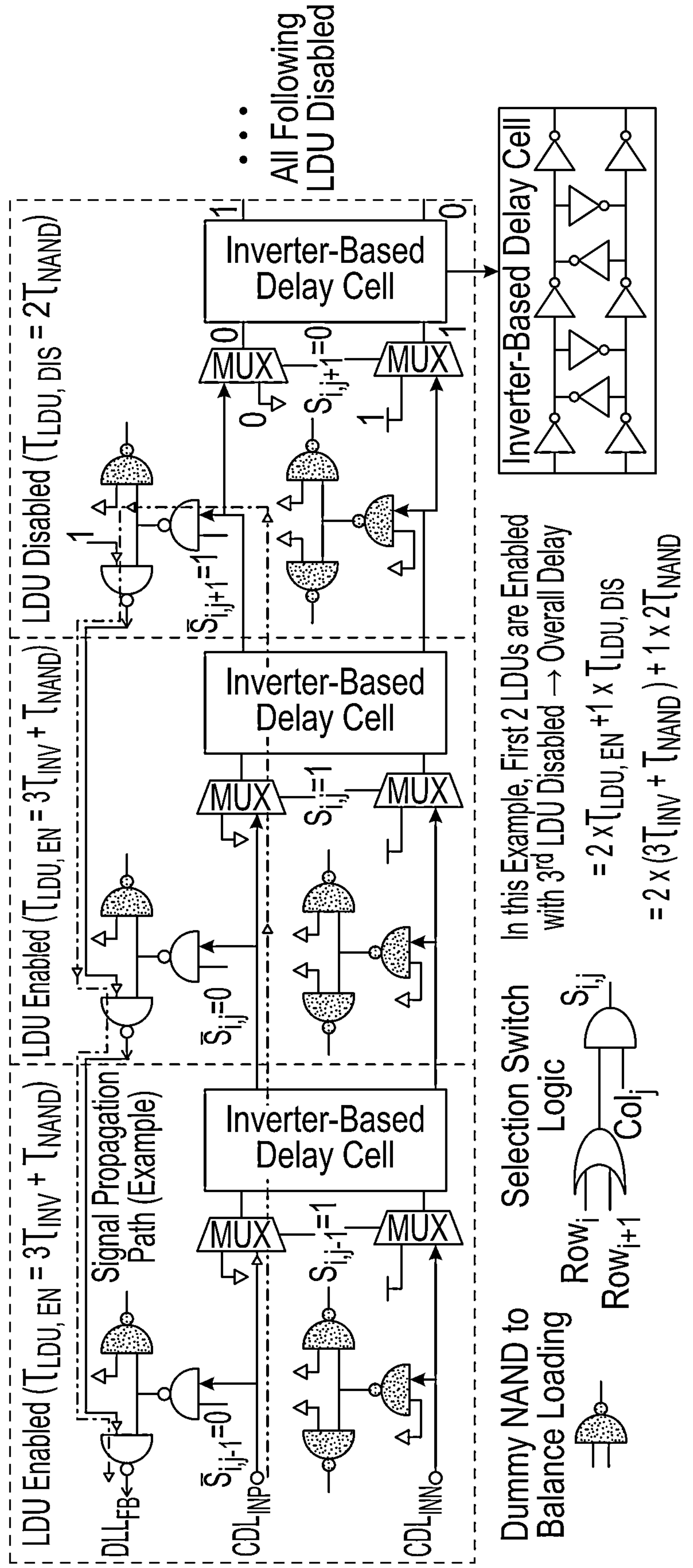
FIG. 7 shows a diagram of schematics of a nested configuration of latticed delay units (LDUs) according to some embodiments.

One limitation of this architecture is its inability to operate in single-shot mode due to the required settling cycles of the SAR. Nevertheless, considering that the frequency of interest for the ICP waveform does not exceed 2 Hz, our TDC settling time (~93 μs) is still fast enough to enable ~10,000 measurements per ICP pulsation. To achieve a high dynamic range, the 8-bit CDL is realized through a nested configuration of 256 cascaded identical lattice delay units (LDUs), as depicted in FIG. 6. The LDUs are distributed in a 2D matrix fashion. The schematic of three consecutive LDUs is shown in FIG. 7. The LDU is implemented using a differential cross-coupled inverter to provide low jitter and filter out any variation in the power supply. As shown in FIG. 7, the signal propagates through the enabled LDUs until it encounters a disabled LDU, at which point the signal propagates back to the first LDU. The total delay of this architecture is given as $$\tau_{CDL} = n\tau_{LDU,EN} + \tau_{LDU,DIS}. \quad (2)$$

In most state-of-the-art delay lines, the entire delay line switches continuously, leading to unnecessary dynamic power consumption. To reduce the power consumption, a multiplexer (MUX) is introduced at the beginning of the delay line, as shown in FIG. 7. If an LDU is disabled (e.g. the third LDU in FIG. 7), the signal propagation is disabled, and no signals propagate to the subsequent LDUs, thereby eliminating unnecessary dynamic power consumption. While the proposed CDL topology can cover a large range, its scalability is potentially hindered by the complexity and size of the 8-bit binary-to-thermometer (8-to-256) decoder required for this relatively long delay line implementation. To address this issue, we propose a new delay line control implementation, i.e., merging the designed delay line with the binary-to-thermometer decoder. Instead of using an 8-to-256 decoder, we use a 4-to-16 row and a 4-to-16 column binary-to-thermometer decoder, as shown in FIG. 6. Each LDU incorporates a selection switch logic. This selection switch logic, based on inputs from the two decoders, enables or disables the LDU. This proposed controlling scheme significantly reduces the complexity of the decoder design.

Figure 8:
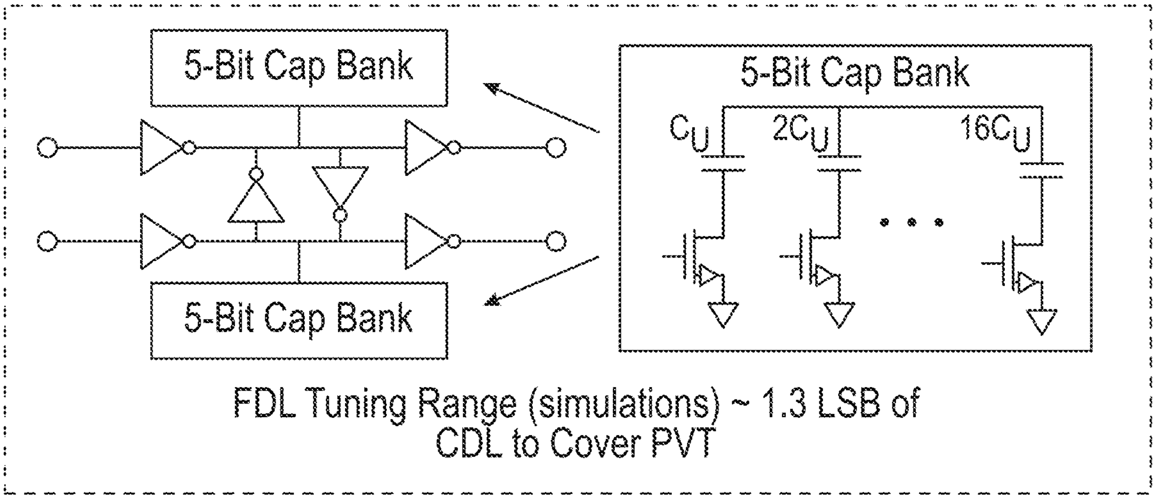
FIG. 8 shows a diagram of a 5-bit delay line according to some embodiments.

To enhance the delay resolution, a 5-bit FDL is employed (see the schematic in FIG. 8). The delay is tuned by a 5-bit capacitor bank.

Initial Tunable Delay

Figure 9:
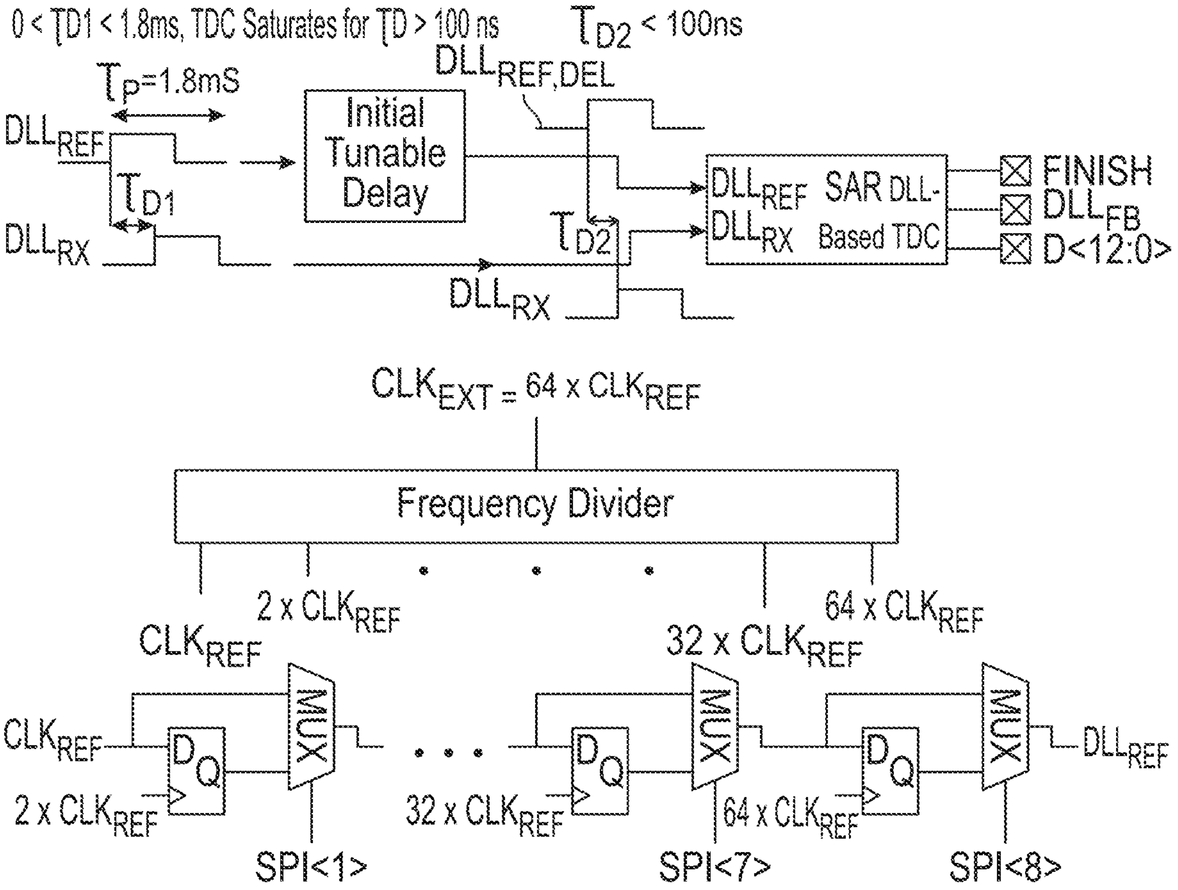
FIG. 9 shows a diagram of an initial tunable delay implementation using DFFs, MUXs, and a frequency divider according to some embodiments.

As the input signal period for the TDC is close to 1.8 μs, significantly exceeding the range the TDC can handle, there is a high chance for the TDC to saturate (see FIG. 9). To prevent TDC saturation, in some embodiments a calibration is performed at the start of the measurement to align $DLL_{REF}$ and $DLL_{RX}$ within the TDC coverage range. This calibration delay needs to cover a range of 1.8 us with a resolution lower than the TDC coverage range. Furthermore, it must contribute minimal jitter to avoid compromising the measurement accuracy. To achieve this, a DFF-based delay is implemented, as shown in FIG. 9. $CLK_{EXT}$ is divided by a factor of 64 to produce $CLK_{REF}$. The intermediate frequencies generated during this division are used to shift $CLK_{REF}$, as illustrated in FIG. 9. An 8-bit SPI is utilized to program the required delay shift. This topology enables signal delay with a resolution of 27.9 ns and a maximum delay of ~1.8 us with minimal jitter contribution. The 27.9-ns resolution is sufficiently small for properly calibrating the TDC at the start of the measurement.

Figure 10:
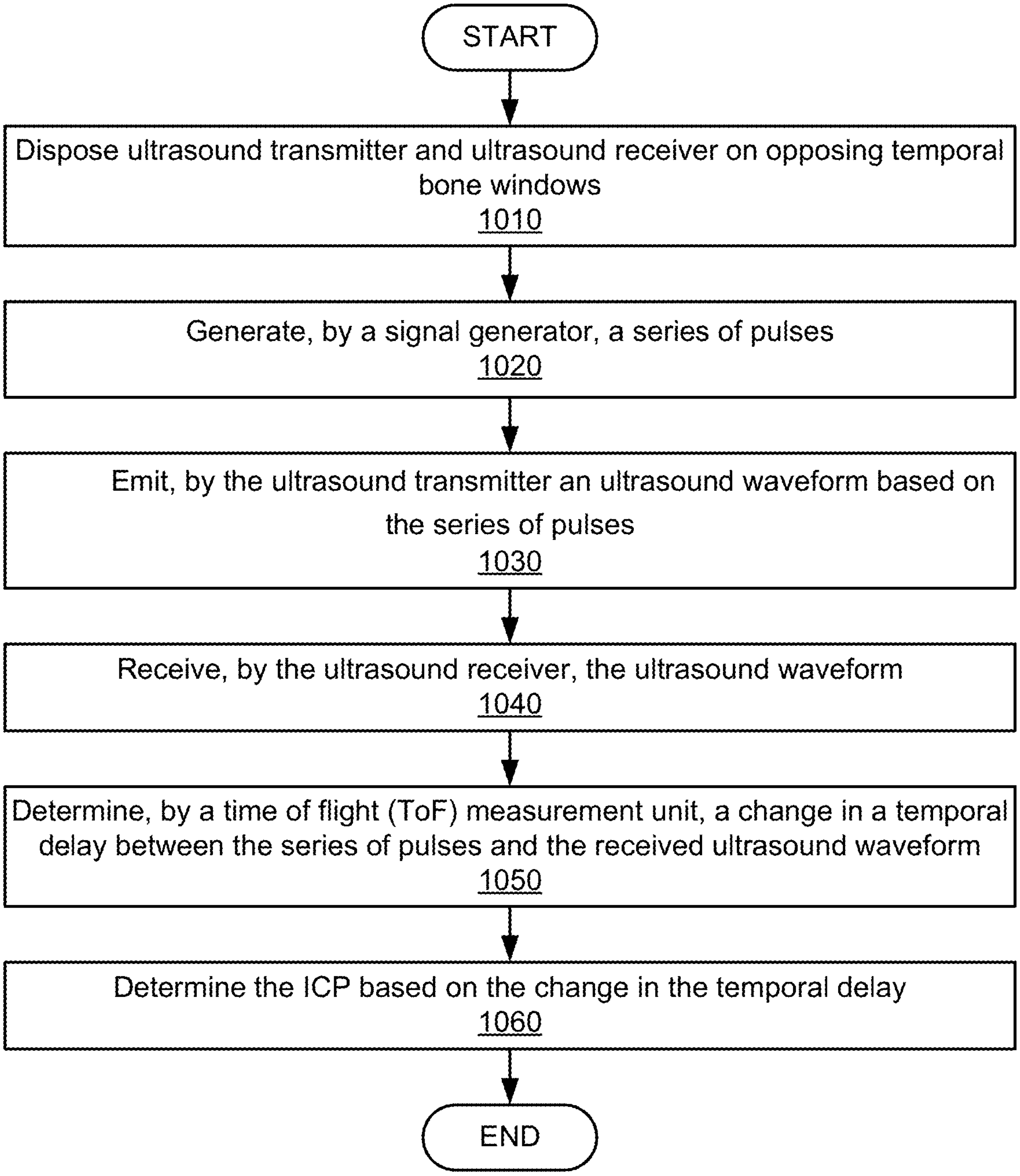
FIG. 10 shows a flowchart of a method according to some embodiments.

Turning to FIG. 10, a flowchart in accordance with one or more embodiments is shown. The flowchart of FIG. 10 depicts a method for non-invasive ICP sensing. The method may be performed using a system as shown in FIGS. 2, 3A, and 3B. One or more of the steps in FIG. 10 may be performed by various components of the system, previously described with reference to FIGS. 2-9.

While the various steps in the flowchart are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively.

In Step 1010, the system is disposed on the patient's head, e.g., with the ultrasound transmitter and the ultrasound receiver aligned to be on the temporal bone windows. Step 1010 may be performed by a clinician, a first responder, etc.

In Step 1020, the signal generator of the system generates a series of pulses as previously described.

In Step 1030, the ultrasound transmitter emits an ultrasound waveform based on the series of pulses. The generation of the ultrasound waveform may be performed as previously described.

In Step 1040, the ultrasound receiver receives the ultrasound waveform. The receiving and processing of the ultrasound waveform may be performed as previously described.

In Step 1050, a change in the temporal delay between the series of pulses and the received ultrasound waveform is determined by a ToF measurement unit. The determining of the change in the temporal delay may be performed as previously described.

In Step 1060, the ICP is determined based on the change in the temporal delay. Measured over time, a qualitative result, e.g., as shown in FIG. 1 may be obtained. An absolute pressure, e.g., an average value of ICP, may be obtained based on transcranial doppler (TCD) and arterial blood pressure (ABP) measurement data. In combination with the method as disclosed, an absolute ICP reading can be obtained over time.

Testing of systems for non-invasive ICP sensing in accordance with embodiments of the disclosure have shown that the system meet the design specifications. Power consumption was found to be 9 mW, thereby enabling a portable or wearable implementation. A resolution of ΔD=45.9 nm was determined, and a good match of measured pressure waveforms with corresponding ground truth pressure waveforms ($R^2$=0.93) was confirmed.

Although the disclosure has been described with respect to only a limited number of embodiments, those skilled in the art, having benefit of this disclosure will appreciate that various other embodiments may be devised without departing from the scope of the present invention. Accordingly, the scope of the invention should be limited only by the attached claims.

What is claimed:

1. A system for non-invasive intracranial pressure (ICP) sensing, comprising:

a signal generator that generates a series of pulses;

an ultrasound transmitter that emits an ultrasound waveform based on the series of pulses;

an ultrasound receiver that receives the ultrasound waveform, wherein a head of a patient is disposed between the ultrasound transmitter and the ultrasound receiver; and a time of flight (ToF) measurement unit configured to determine a change in a temporal delay between the series of pulses and the received ultrasound waveform, wherein the ToF measurement unit comprises a time-to-digital converter (TDC), wherein the TDC is a successive approximation register (SAR) DLL-based TDC and comprises a coarse delay line, a fine delay line, and a phase detector, and wherein the coarse delay line comprises a plurality of cascaded lattice delay units (LDUs) distributed in a 2D matrix with row and column binary-to-thermometer decoders.

2. The system of claim 1, wherein the signal generator is a constant frequency signal generator.

3. The system of claim 1, further comprising a power amplifier configured to drive the ultrasound transmitter based on the series of pulses.

4. The system of claim 3, wherein the power amplifier is a Class-DE power amplifier.

5. The system of claim 4, wherein the Class-DE power amplifier comprises a first switch and a second switch, both implemented using cascode switches to double a supply voltage.

6. The system of claim 3, further comprising a matching network disposed between the power amplifier and the ultrasound transmitter, wherein the matching network is configured to down-convert an impedance of the ultrasound transmitter.

7. The system of claim 1, wherein the ToF measurement unit further comprises an initial tunable delay configured to delay an input of the TDC.

8. The system of claim 1, wherein the system is wearable.

9. A method for non-invasive intracranial pressure (ICP) sensing, comprising:

generating, by a signal generator, a series of pulses;

emitting, by an ultrasound transmitter an ultrasound waveform based on the series of pulses;

receiving, by an ultrasound receiver, the ultrasound waveform, wherein a head of a patient is disposed between the ultrasound transmitter and the ultrasound receiver; and determining, by a time of flight (ToF) measurement unit, a change in a temporal delay between the series of pulses and the received ultrasound waveform, wherein the ToF measurement unit comprises a successive approximation register (SAR DLL-based time-to-digital converter (TDC), wherein the TDC comprises a coarse delay line, a fine delay line, and a phase detector, and wherein the coarse delay line comprises a plurality of cascaded lattice delay units (LDUs) distributed in a 2D matrix with row and column binary-to-thermometer decoders.

10. The method of claim 9, further comprising determining the ICP based on the change in the temporal delay.

11. The method of claim 9, further comprising disposing the ultrasound transmitter and the ultrasound receiver on opposing temporal bone windows.

12. The method of claim 9, further comprising driving, by a Class-DE power amplifier, the ultrasound transmitter based on the series of pulses, wherein the Class-DE power amplifier comprises a first switch and a second switch, both implemented using cascode switches to double a supply voltage.

13. The method of claim 9, further comprising delaying by an initial tunable delay, an input of the TDC.

* * * * *